United States Patent
Jambor et al.

(10) Patent No.: US 7,618,365 B2
(45) Date of Patent: *Nov. 17, 2009

(54) METHOD OF IMPLATING A MEDICAL DEVICE USING A SUTURE TAB EXTENDER

(75) Inventors: Kristin L. Jambor, Cincinnati, OH (US); Jeffrey P. Wiley, Cincinnati, OH (US); Lauren S. Weaner, Beavercreek, OH (US); Dustin R. Jensen, Loveland, OH (US); Patrick J. Swindon, Cincinnati, OH (US); Christopher W. Widenhouse, Clarksville, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 299 days.

This patent is subject to a terminal disclaimer.

(21) Appl. No.: 11/489,752

(22) Filed: Jul. 20, 2006

(65) Prior Publication Data

US 2007/0173685 A1 Jul. 26, 2007

Related U.S. Application Data

(63) Continuation-in-part of application No. 11/182,072, filed on Jul. 15, 2005, now Pat. No. 7,416,528, and a continuation-in-part of application No. 11/364,362, filed on Mar. 1, 2006, now Pat. No. 7,367,937, which is a continuation-in-part of application No. 11/364,361, filed on Mar. 1, 2006, now Pat. No. 7,364,542, which is a continuation-in-part of application No. 11/364,363, filed on Mar. 1, 2006.

(60) Provisional application No. 60/699,369, filed on Jul. 15, 2005.

(51) Int. Cl.
*A61F 2/00* (2006.01)

(52) U.S. Cl. .......................................... 600/37

(58) Field of Classification Search ............. 600/29–32, 600/37; 128/897–898; 606/151–158, 201–203
See application file for complete search history.

(56) References Cited

U.S. PATENT DOCUMENTS

| 4,510,649 A | 4/1985 | Yudis et al. |
| 4,592,339 A | 6/1986 | Kuzmak et al. |

(Continued)

FOREIGN PATENT DOCUMENTS

EP 1319371 A2 6/2003

(Continued)

*Primary Examiner*—John P Lacyk

(57) ABSTRACT

A method of implanting a surgically implantable band, the method comprising the steps of providing a band with an elongated body member having a first end with a first latching member positioned thereon, and a second end with a second latching member positioned thereon. The first latching member has a suture tab extender extending therefrom. The suture tab extender has a suture attached thereto. The second end has a gripping section positioned thereon shaped and dimensioned to facilitate gripping as the gastric band extender is passed through the second latching member. The method further includes the step of positioning the band around an anatomical structure and latching the band around the structure by placing the suture tab extender through the second latching member and thereafter coupling the first and second latching members. The method further involves the step of removing the suture tab extender from the band.

5 Claims, 12 Drawing Sheets

U.S. PATENT DOCUMENTS

| | | | |
|---|---|---|---|
| 4,696,288 | A | 9/1987 | Kuzmak et al. |
| 4,760,837 | A | 8/1988 | Petit |
| 5,033,481 | A | 7/1991 | Heyler, III |
| 5,065,772 | A | 11/1991 | Cox, Jr. |
| 5,074,868 | A | 12/1991 | Kuzmak |
| 5,078,676 | A | 1/1992 | Bailly |
| 5,083,576 | A | 1/1992 | Ruiz-Razura et al. |
| 5,160,338 | A | 11/1992 | Vincent |
| 5,226,426 | A | 7/1993 | Yoon |
| 5,226,429 | A | 7/1993 | Kuzmak |
| 5,601,604 | A | 2/1997 | Vincent |
| 5,658,298 | A | 8/1997 | Vincent et al. |
| RE36,176 | E | 3/1999 | Kuzmak |
| 5,910,149 | A | 6/1999 | Kuzmak |
| 5,938,669 | A | 8/1999 | Klaiber et al. |
| 6,067,991 | A | 5/2000 | Forsell |
| 6,102,922 | A | 8/2000 | Jakobsson et al. |
| 6,210,347 | B1 | 4/2001 | Forsell |
| 6,450,173 | B1 | 9/2002 | Forsell |
| 6,450,946 | B1 | 9/2002 | Forsell |
| 6,453,907 | B1 | 9/2002 | Forsell |
| 6,454,698 | B1 | 9/2002 | Forsell |
| 6,454,699 | B1 | 9/2002 | Forsell |
| 6,454,700 | B1 | 9/2002 | Forsell |
| 6,454,701 | B1 | 9/2002 | Forsell |
| 6,460,543 | B1 | 10/2002 | Forsell |
| 6,461,292 | B1 | 10/2002 | Forsell |
| 6,461,293 | B1 | 10/2002 | Forsell |
| 6,463,935 | B1 | 10/2002 | Forsell |
| 6,464,628 | B1 | 10/2002 | Forsell |
| 6,464,928 | B1 | 10/2002 | Lipukin et al. |
| 6,470,892 | B1 | 10/2002 | Forsell |
| 6,471,635 | B1 | 10/2002 | Forsell |
| 6,475,136 | B1 | 11/2002 | Forsell |
| 6,482,145 | B1 | 11/2002 | Forsell |
| 6,503,189 | B1 | 1/2003 | Forsell |
| 6,511,490 | B2 | 1/2003 | Robert |
| 6,547,801 | B1 | 4/2003 | Dargent et al. |
| 6,676,674 | B1 | 1/2004 | Dudai |
| 6,709,385 | B2 | 3/2004 | Forsell |
| 6,915,165 | B2 | 7/2005 | Forsell |
| 6,916,326 | B2 | 7/2005 | Benchetrit |
| 6,953,429 | B2 | 10/2005 | Forsell |
| 6,966,875 | B1 | 11/2005 | Longobardi |
| 7,011,624 | B2 | 3/2006 | Forsell |
| 7,364,542 | B2 * | 4/2008 | Jambor et al. ............ 600/37 |
| 2003/0019498 | A1 | 1/2003 | Forsell |
| 2003/0032857 | A1 | 2/2003 | Forsell |
| 2003/0066536 | A1 | 4/2003 | Forsell |
| 2003/0092962 | A1 | 5/2003 | Forsell |
| 2003/0105385 | A1 | 6/2003 | Forsell |
| 2003/0114729 | A1 | 6/2003 | Forsell |
| 2003/0158564 | A1 | 8/2003 | Benchetrit |
| 2004/0049209 | A1 | 3/2004 | Benchetrit |
| 2004/0153106 | A1 | 8/2004 | Dudai |
| 2004/0158272 | A1 | 8/2004 | Hofle et al. |
| 2004/0230137 | A1 | 11/2004 | Mouton |
| 2004/0254536 | A1 | 12/2004 | Conlon et al. |
| 2004/0254537 | A1 | 12/2004 | Conlon et al. |
| 2004/0260319 | A1 | 12/2004 | Egle |
| 2004/0267288 | A1 | 12/2004 | Byrum et al. |
| 2004/0267291 | A1 | 12/2004 | Byrum et al. |
| 2004/0267292 | A1 | 12/2004 | Byrum et al. |
| 2004/0267293 | A1 | 12/2004 | Byrum et al. |
| 2005/0002984 | A1 | 1/2005 | Byrum et al. |
| 2005/0038458 | A1 | 2/2005 | Bailly et al. |
| 2005/0070937 | A1 | 3/2005 | Jambor et al. |
| 2005/0119672 | A1 | 6/2005 | Benchetrit |
| 2005/0119674 | A1 | 6/2005 | Gingras |
| 2005/0183730 | A1 | 8/2005 | Byrum |
| 2005/0187566 | A1 | 8/2005 | Byrum |
| 2005/0277963 | A1 | 12/2005 | Fields |
| 2005/0283041 | A1 | 12/2005 | Egle |
| 2006/0074439 | A1 | 4/2006 | Garner et al. |
| 2007/0016229 | A1 | 1/2007 | Jambor et al. |

FOREIGN PATENT DOCUMENTS

| | | |
|---|---|---|
| EP | 1491168 A1 | 12/2004 |
| EP | 1598020 A1 | 11/2005 |
| EP | 1607072 B1 | 8/2007 |
| EP | 1645249 B1 | 5/2008 |
| EP | 1743606 B1 | 3/2009 |
| FR | 2846877 A1 | 11/2002 |
| WO | 86/04498 A1 | 8/1986 |
| WO | 03/059215 A1 | 7/2003 |
| WO | 2004/108025 A1 | 12/2004 |
| WO | 2005/072195 A2 | 8/2005 |
| WO | 2005/072664 A1 | 8/2005 |

* cited by examiner

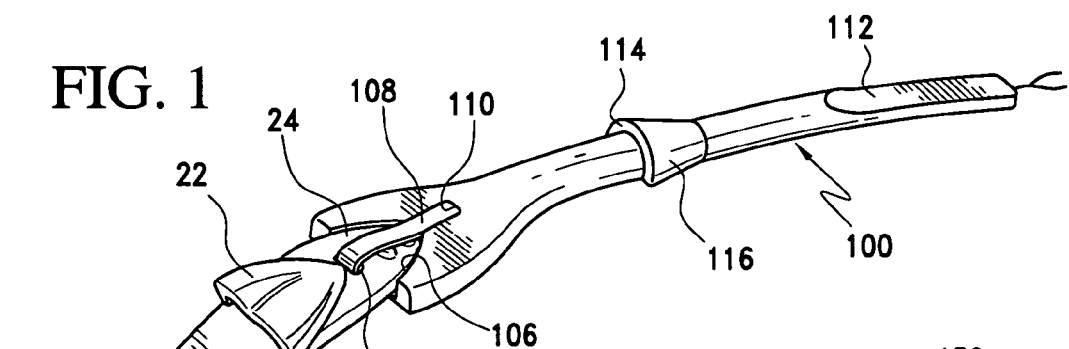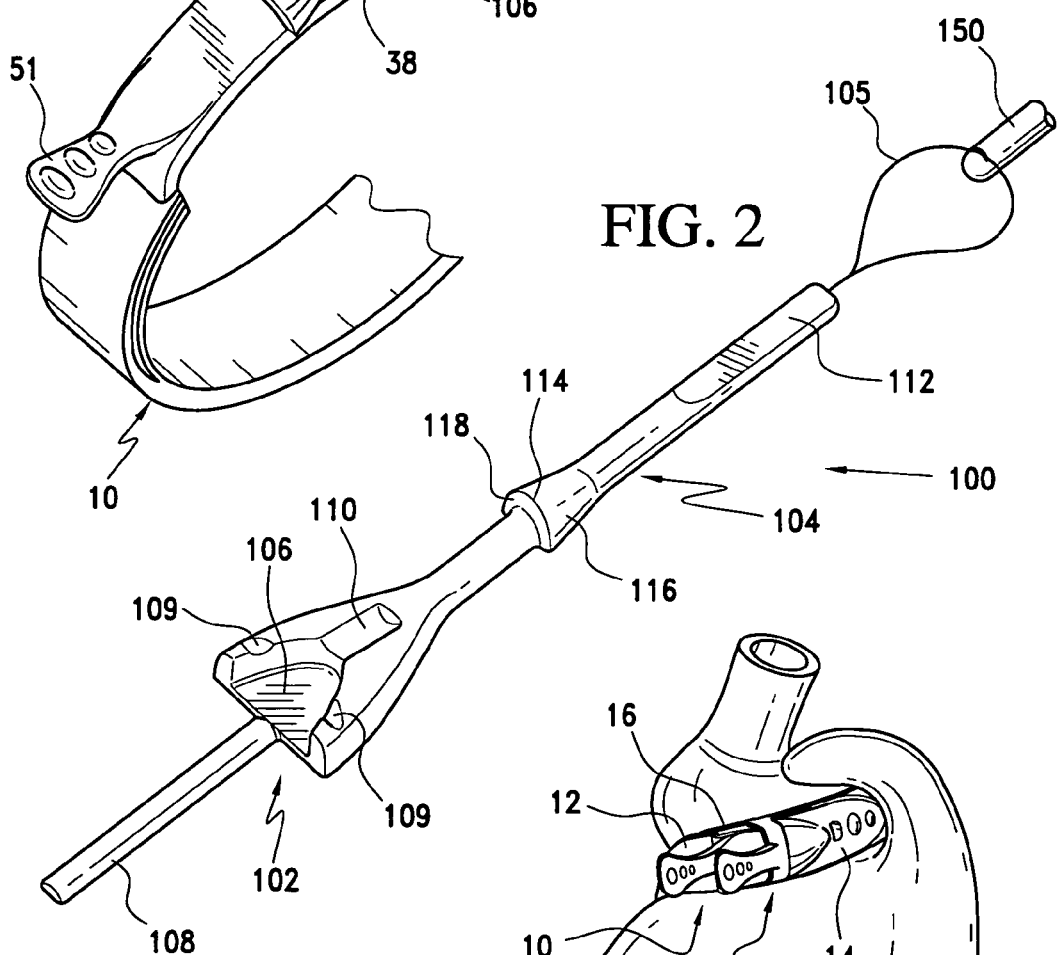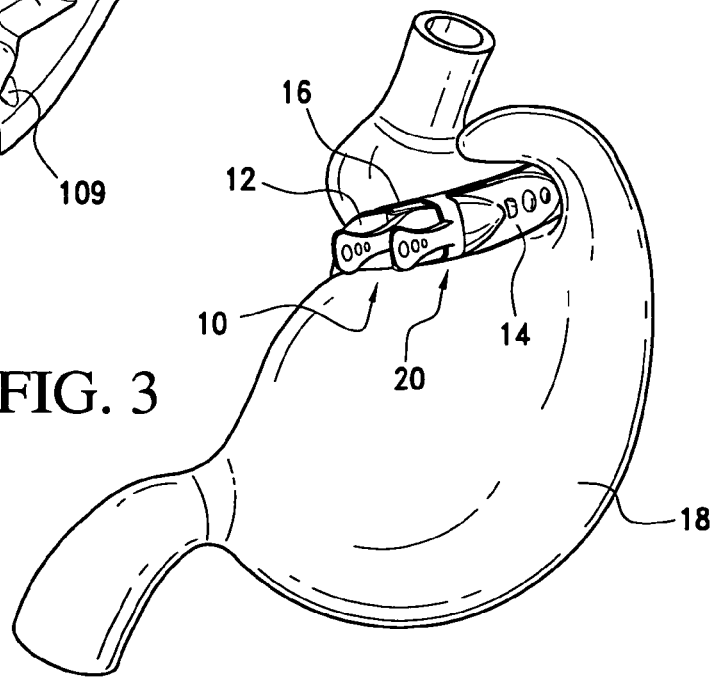

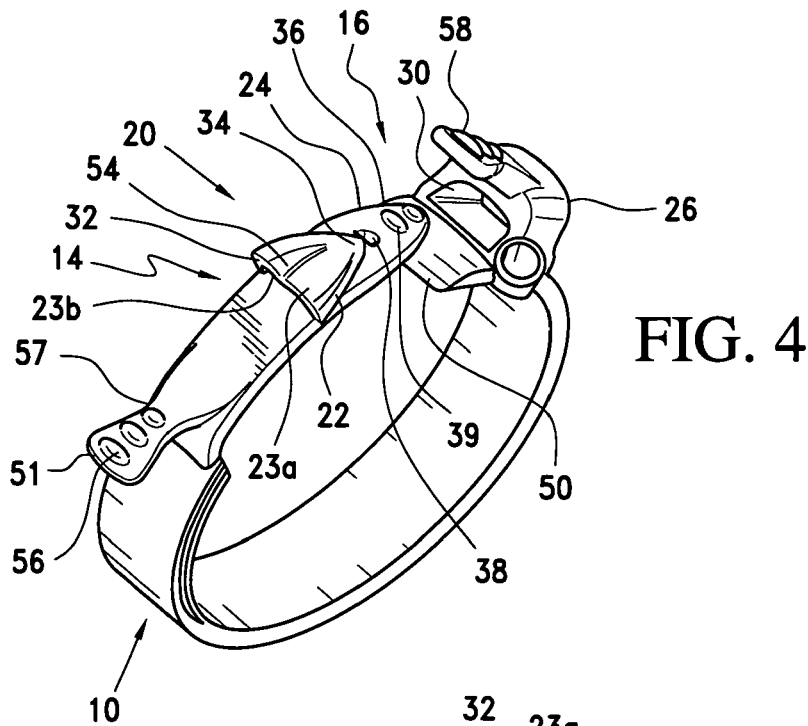
FIG. 4
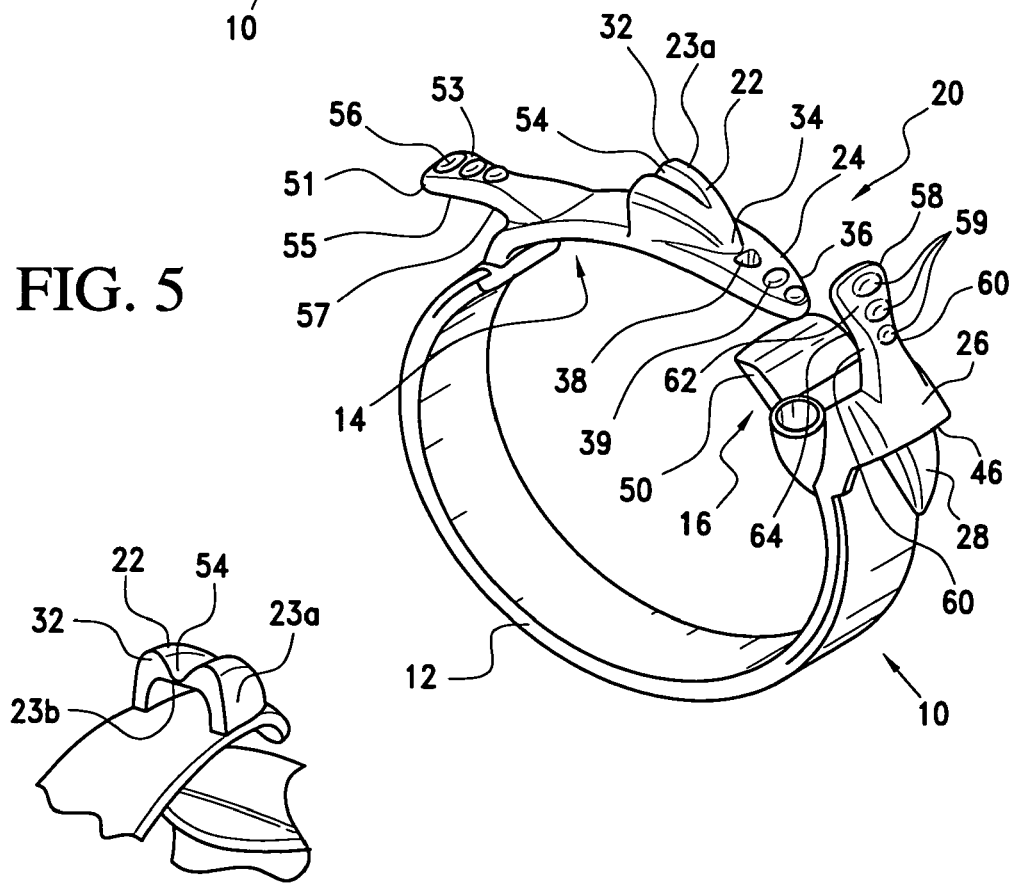
FIG. 5
FIG. 5a

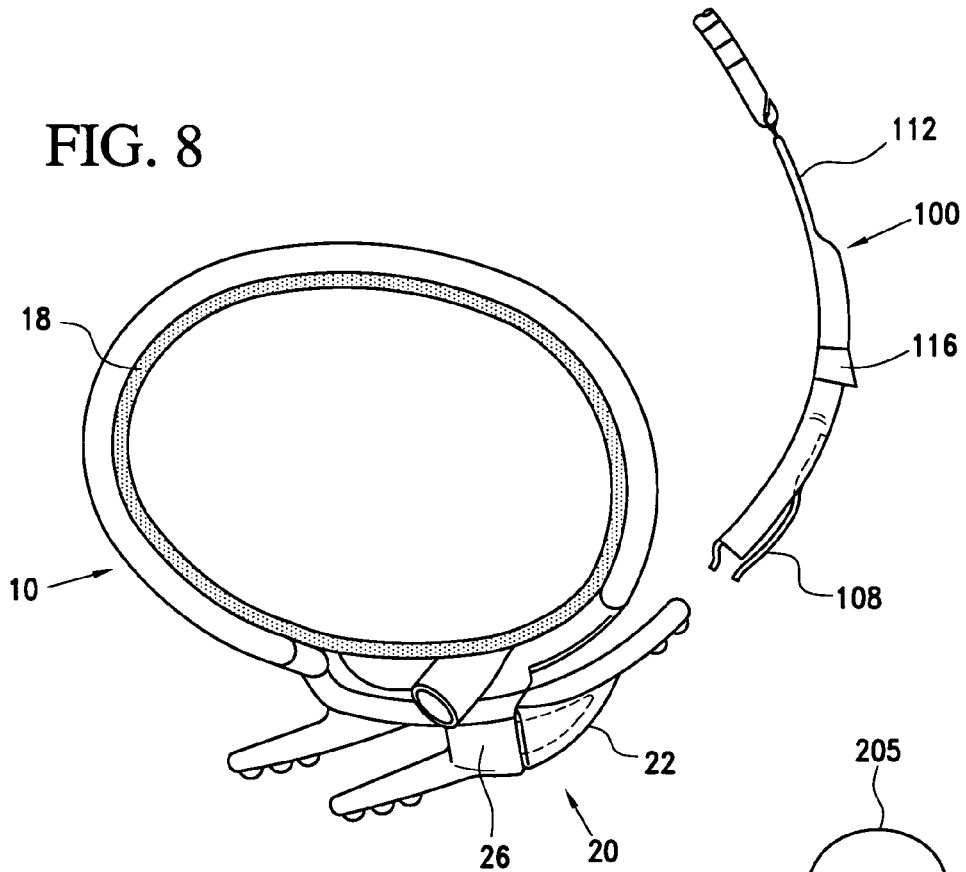
FIG. 8
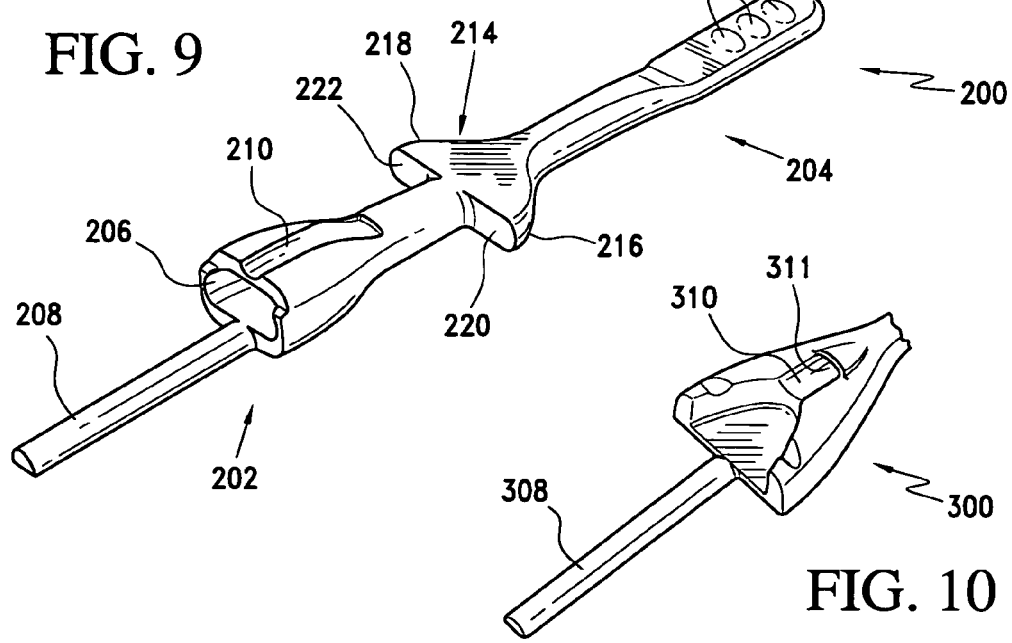
FIG. 9
FIG. 10

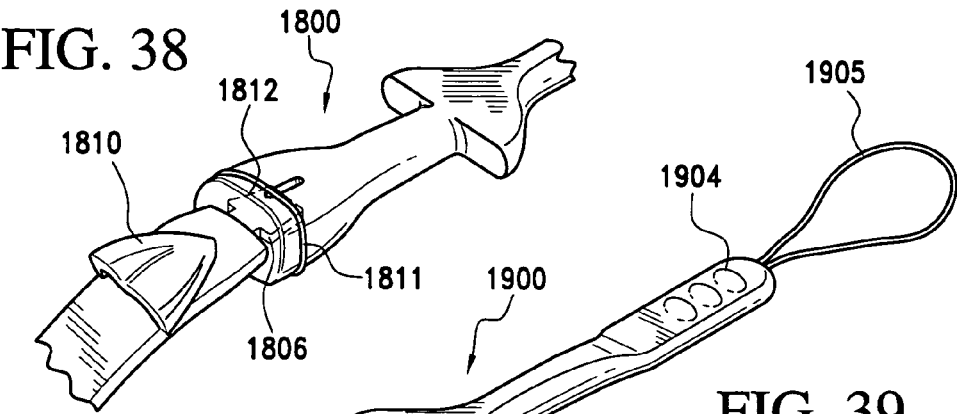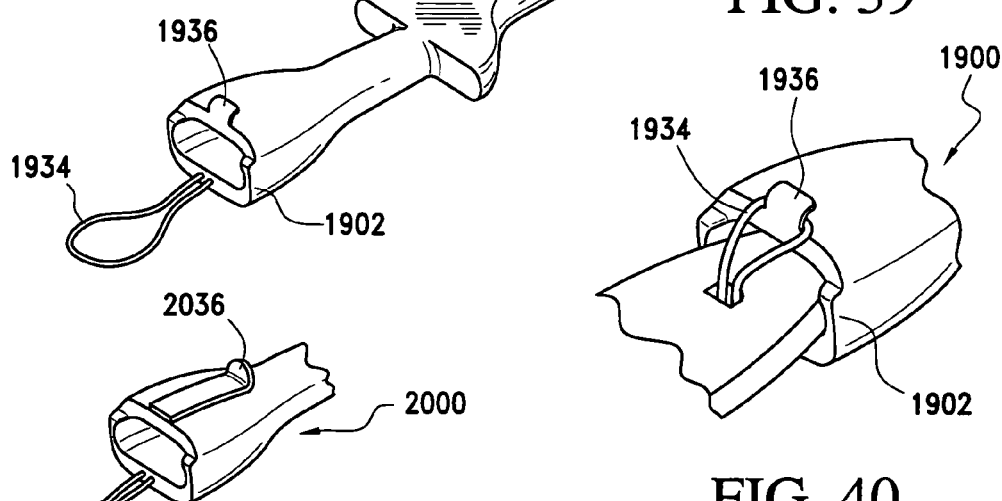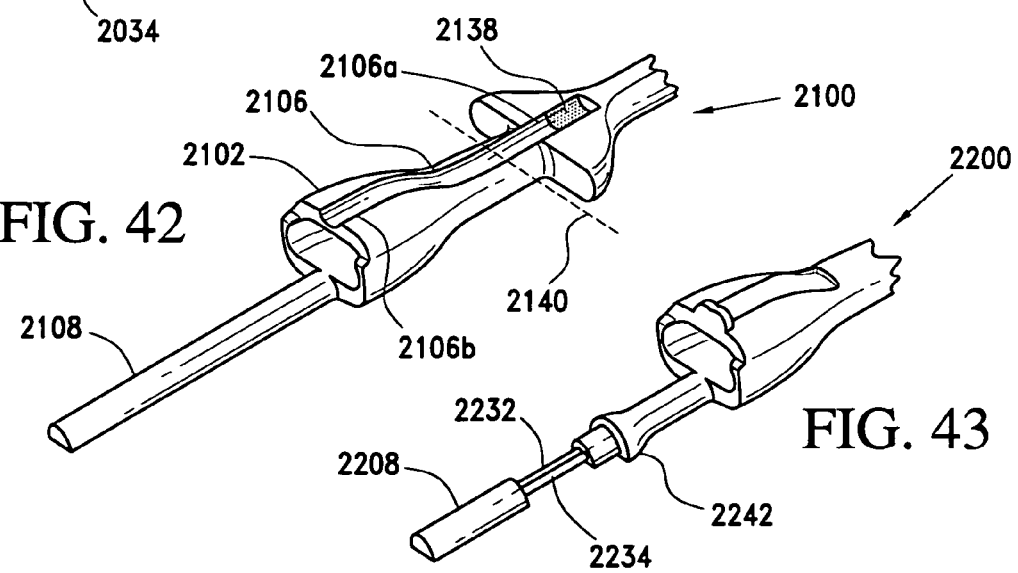

METHOD OF IMPLATING A MEDICAL DEVICE USING A SUTURE TAB EXTENDER

CROSS REFERENCE TO RELATED APPLICATIONS

This application is a continuation in part of U.S. patent application Ser. No. 11/182,072, entitled "LATCHING DEVICE FOR GASTRIC BAND", filed Jul. 15, 2005 now U.S. Pat. No. 7,416,528, and claims the benefit of U.S. Provisional Application Ser. No. 60/699,369, entitled "GASTRIC BAND", filed Jul. 15, 2005. This application is a continuation in part of U.S. patent application Ser. No. 11/364,362 entitled "GASTRIC BAND", filed Mar. 1, 2006 now U.S. Pat. No. 7,367,937, which is a continuation in part of U.S. patent application Ser. No. 11/364,361 entitled "GASTRIC BAND SUTURE TAB EXTENDER", Filed on Mar. 1, 2006 now U.S. Pat. No. 7,364,542, which is a continuation in part of U.S. patent application Ser. No. 11/364,363 entitled "Pre-curved Gastric Band", filed on Mar. 1, 2006.

BACKGROUND OF THE INVENTION

1. Field of the Invention

The invention relates to a gastric band and related accessories.

2. Description of the Prior Art

Morbid obesity is a serious medical condition. In fact, morbid obesity has become highly pervasive in the United States, as well as other countries, and the trend appears to be heading in a negative direction. Complications associated with morbid obesity include hypertension, diabetes, coronary artery disease, stroke, congestive heart failure, multiple orthopedic problems and pulmonary insufficiency with markedly decreased life expectancy. With this in mind, and as those skilled in the art will certainly appreciate, the monetary and physical costs associated with morbid obesity are substantial. In fact, it is estimated the costs relating to obesity are in excess of one hundred billion dollars in the United States alone.

A variety of surgical procedures have been developed to treat obesity. The most common currently performed procedure is Roux-en-Y gastric bypass (RYGB). This procedure is highly complex and is commonly utilized to treat people exhibiting morbid obesity. Other forms of bariatric surgery include Fobi pouch, bilio-pancreatic diversion, and gastro-plastic or "stomach stapling". In addition, implantable devices are known which limit the passage of food through the stomach and affect satiety.

In view of the highly invasive nature of many of these procedures, efforts have been made to develop less traumatic and less invasive procedures. Gastric-banding is one of these methods. Gastric-banding is a type of gastric reduction surgery attempting to limit food intake by reducing the size of the stomach. In contrast to RYGB and other stomach reduction procedures, gastric-banding does not require the alteration of the anatomy of the digestive tract in the duodenum or jejunum.

Since the early 1980's, gastric bands have provided an effective alternative to gastric bypass and other irreversible surgical weight loss treatments for the morbidly obese. Several alternate procedures are performed under the heading of gastric-banding. Some banding techniques employ a gastric ring, others use a band, some use stomach staples and still other procedures use a combination of rings, bands and staples. Among the procedures most commonly performed are vertical banded gastroplasty (VBG), silastic ring gastroplasty (SRG) and adjustable silastic gastric banding (AGB).

In general, the gastric band is wrapped around an upper portion of the patient's stomach, forming a stoma that is less than the normal interior diameter of the stomach. This restricts food passing from an upper portion to a lower digestive portion of the stomach. When the stoma is of an appropriate size, food held in the upper portion of the stomach provides a feeling of fullness that discourages over eating.

More particularly, and in practice, the gastric band is inserted behind the stomach and the ends of the gastric band are coupled to latch the device about the stomach. However, it is often difficult to maneuver the ends of the gastric band for proper latching. As such, mechanisms for enhancing the application of gastric bands about a stomach are needed. The present invention provides such a mechanism in the form of an extension device for utilization in conjunction with currently available gastric bands, which is removable after the gastric band is properly installed. The present invention also provides an improved gastric band construction facilitating ease of application about a stomach and enhanced functionality once applied.

SUMMARY OF THE INVENTION

In accordance with the present invention, there is provided a method of implanting a surgically implantable band, the method comprising the steps of providing a band with an elongated body member having a first end with a first latching member positioned thereon, and a second end with a second latching member positioned thereon. The first latching member has a suture tab extender extending therefrom. The suture tab extender has a suture attached thereto. The second end has a gripping section positioned thereon shaped and dimensioned to facilitate gripping as the gastric band extender is passed through the second latching member. The method further includes the step of positioning the band around an anatomical structure and latching the band around the structure by placing the suture tab extender through the second latching member and thereafter coupling the first and second latching members. The method further involves the step of removing the suture tab extender from the band.

BRIEF DESCRIPTION OF THE DRAWINGS

FIG. 1 is a perspective view of the suture tab extender secured to a gastric band.

FIG. 2 is a perspective view of the removable suture tab extender.

FIG. 3 is a perspective view of the gastric band secured about the stomach.

FIGS. 4, 5 and 5a are various perspective views of a gastric band in accordance with the present invention.

FIGS. 6, 7 and 8 show the various steps in the attachment of the gastric band using the present suture tab extender.

FIG. 9 is a perspective view of a suture tab extender in accordance with a further embodiment.

FIG. 10 is a perspective view of a suture tab extender in accordance with an alternate embodiment.

FIGS. 32 to 43 show various embodiments of suture tab extenders with differing attachment structures.

DESCRIPTION OF THE PREFERRED EMBODIMENTS

Figure 6:
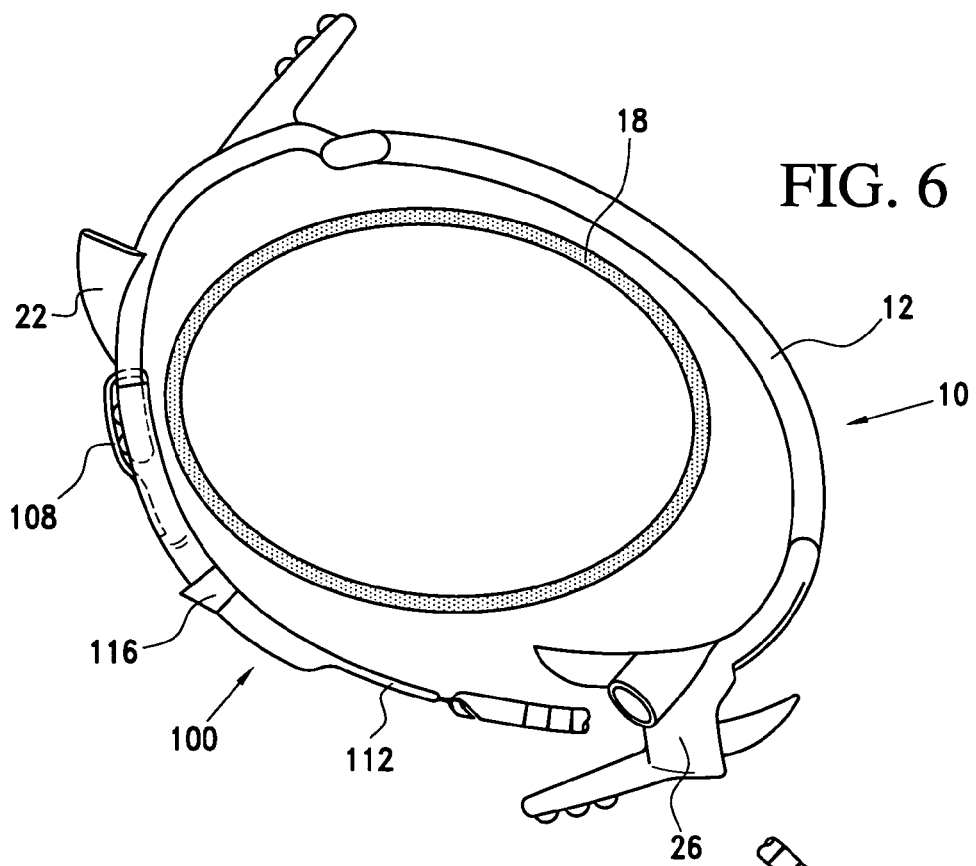
Figure 7:
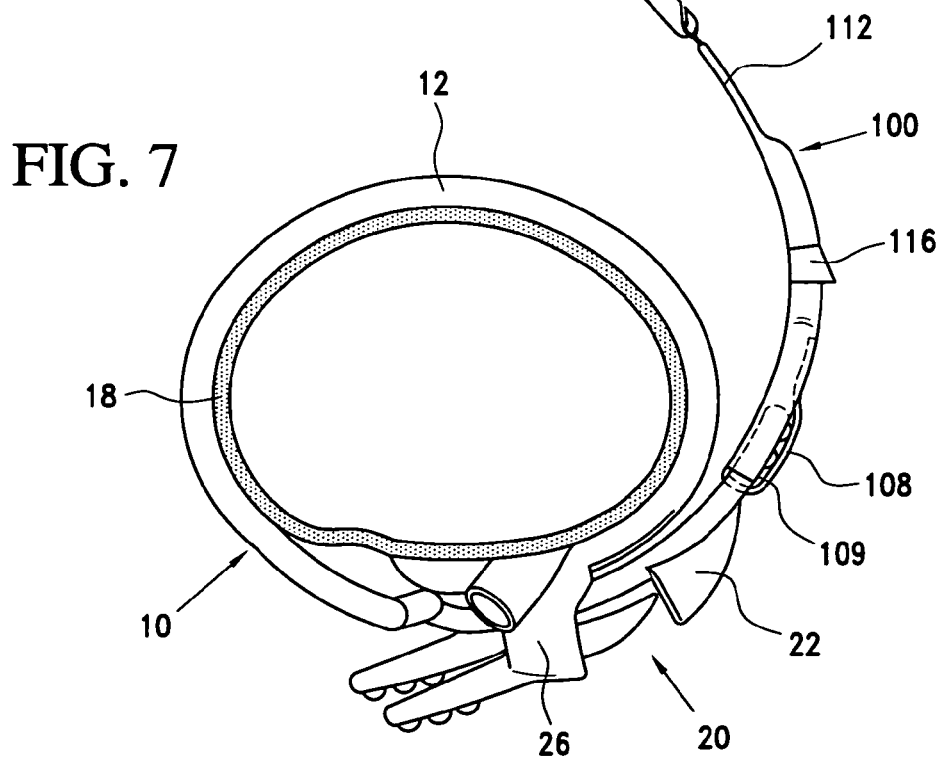
Figure 11:
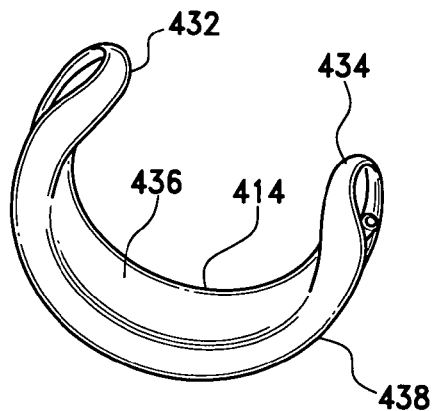
FIGS. 11, 12, 13 and 14 respectively show a perspective view of a balloon, a perspective view of a belt, a cross sectional view of a gastric band and a perspective view of the gastric band in accordance with another embodiment of the present invention.
Figure 12:
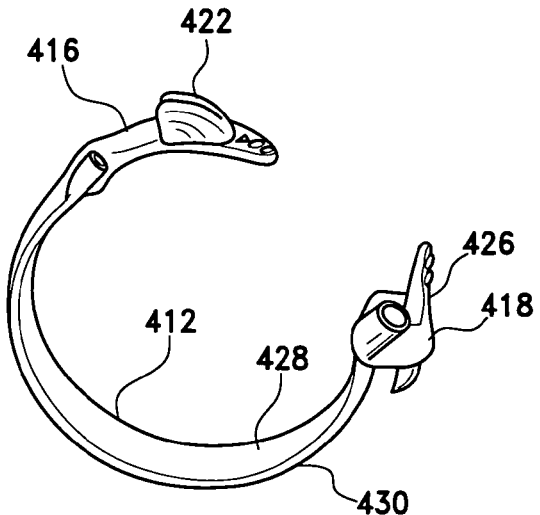
Figure 13:
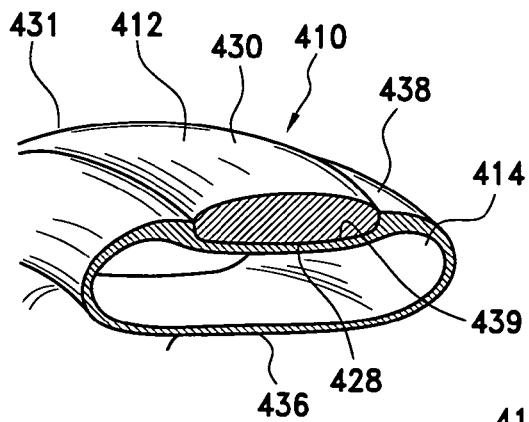
Figure 14:
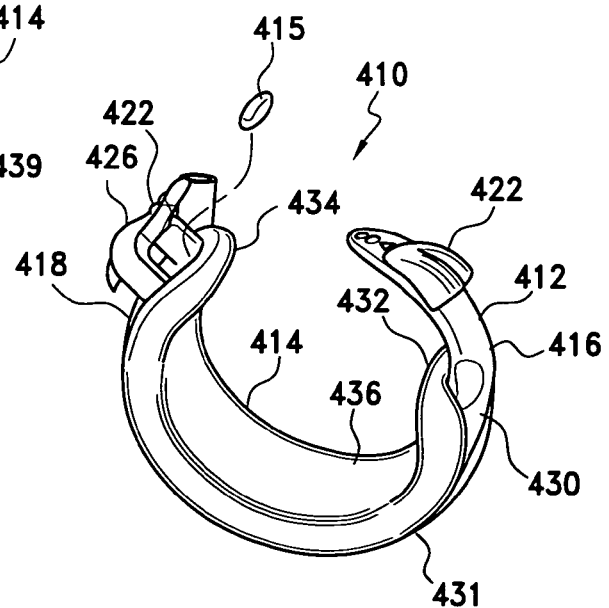

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for the claims and for teaching one skilled in the art how to make and/or use the invention.

With reference to FIGS. 1 and 2, a removable suture tab extender 100 for use in conjunction with a gastric band 10 is disclosed. The extender 100 is designed to enhance usage of gastric bands 10 and aid with the use of the gastric band latching mechanism 20. In particular, the extender 100 provides a mechanism for assisting in the passage of the first latching member 22 of the latching mechanism 20 through the second latching member 26 of the latching mechanism 20 by either threading or pushing the first latching member 22 through the second latching member 26 or by inserting a grasper through the second latching member 26, grasping the tip of the extender 112, and pulling it back through the second latching member 26 to lock.

To attach the extender 100 to the gastric band 10, the tether strap 108 of the extender 100 is threaded through an aperture 38 in the tip of the latching mechanism 20. This tether strap 108 is then glued to the rest of the extender 100 inside a coupling indent 110. In accordance with an alternate embodiment, and with reference to FIG. 10, the extender 300 may be provided with a pocket 311 positioned at the end of the coupling indent 310 in which the tether strap 308 may be glued.

The extender 100 is easily removed or cut apart from the gastric band 10 once the gastric band 10 is properly positioned and secured about the stomach, thereby minimizing the risk of "sharp" band edges if the band itself was cut. To remove the extender 100, the tether strap 108 is cut between the aperture 38 in the tip 36 of the gastric band 20 and the coupling indent 110 containing the glued tether strap 108. This allows the extender 100 to be removed in one piece, leaving the gastric band 100 completely intact without any "sharp" band edges.

The extender 100 may further be provided with a recess 109 (see FIG. 2) on the extender 100 for inserting scissors between the tip 36 of the gastric band 20 and the tether strap 108 to better facilitate cutting off the extender 100. The extender 100 is completely removed from the body after it has been cut off of the gastric band 10. The extender 100 also allows for the creation of an interim lock permitting adjustment around the stomach before final locking of the latching mechanism 20. Although a preferred embodiment has the extender cut off for one piece removal from the gastric band body, an alternate embodiment would entail leaving the extender in place on the gastric band and utilizing the interim lock (that is, the retention member 114, 214 that is described below in greater detail) as an additional permanent locking position for use with varying stomach sizes.

In practice, and with reference to FIG. 3, the present suture tab extender 100 is secured to the first end 14 of the gastric band 10 adjacent the first latching member 22 to form a single band/extender functional unit. Thereafter, the gastric band 10, with the extender 100 secured thereto, is inserted behind the stomach. The first latching member 22 of the latching mechanism 20, as well as the extender 100, are then pushed or pulled through the second latching member 26 of the latching mechanism 20. The addition of the present suture tab extender 100 provides a longer region for grasping and manipulation of the first latching member 22 as it is passed about the stomach and through the second latching member 26.

In accordance with a preferred embodiment, and as will be discussed below in greater detail, the suture tab extender 100 is an elongated, elastomeric component that attaches to the first end 14 of the gastric band 10 to assist in mating and locking the first latching member 22 with the second latching member 26. The extender 100 is preferably attached to a tab 24 at the first end 14 of the gastric band 10 to hold the extender 100 in place. The extender 100 is removable with one cut through the tether strap 108 on the extender 100 and incorporates a recess or an open recess, for example, a cuplike feature, 106 for coupling the first end 14 of gastric band 10 and extender 100 close together so as to move as an integral unit.

More specifically, and as will be greater appreciated based upon the following disclosure, the tab 24 of the gastric band 10 is positioned within the recess 106 of the extender 100 and is safely and securely coupled thereto using a tether strap 108. In addition, and in accordance with the preferred embodiment, the second end of the extender may include a suture loop 105 for compatibility with a Goldfinger-like device 150. As those skilled in the art will certainly appreciate, the Goldfinger-like device 150 assists in passing the gastric band 20 through the retro-gastric tunnel. Alternately, for surgeons who use other devices for passing the gastric band 20 through the retro-gastric tunnel, the gripping section, or flat tip, 112 of the extender 100 is compatible with these band-passing devices as well. In general a Goldfinger instrument is an articulating band passing device used to perform blunt dissection behind the stomach before passing the gastric band. It is articulated and fed behind the stomach. In the tip of the Goldfinger instrument there is a notch that a suture loop can catch on. Once the suture is caught, the Goldfinger instrument is pulled out of the retro-gastric tunnel and the suture loop pulls the band with it. Alternately, to facilitate use with these other band passing-devices, a length of the extender may be round (like tubing) behind the flat tip so that the extender is easier to orient.

The removable extender 100 is designed for use with a variety of gastric bands. By way of example, the extender is designed for use with gastric bands as disclosed in commonly owned U.S. patent application Ser. No. 11/182,072, filed Jul. 15, 2005, entitled "LATCHING DEVICE FOR GASTRIC BAND", which is incorporated herein by reference.

In general, and with reference to FIGS. 4, 5 and 5a, the gastric band 10 includes a band body 12 having a first end 14 and a second opposite end 16. The band body 12 and latching mechanism 20 are preferably manufactured from silicone. Although, and as will be discussed below in greater detail, the gastric band is a balloon type gastric band, the present latching mechanism may be used in conjunction with a variety of band structures without departing from the spirit of the present invention.

As briefly mentioned above, the gastric band 10 is shaped and dimensioned to circumscribe the stomach at a predetermined location reducing the size of the stomach. The gastric band 10 employs a flexible latching mechanism 20 capable of locking and unlocking without destruction of the latching mechanism 20 or significant reduction in retention capabilities after re-locking. The first and second ends 14, 16 respectively act as both male and female members depending on the direction of motion and intent to lock or unlock the latching mechanism 20 of the present gastric band 10.

The first end 14 includes a shell member, or first latching member, 22 generally composed of a hollow, half-moon shaped shell with a tab 24 for gripping and pulling through a collar member, or second latching member, 26 composed of a semi-circular shaped aperture 30 on the second end 16. The half-moon shell of the first latching member 22 collapses as it is pulled or pushed through the collar member 26 by a grasper. The collar member 26 includes a tongue 28 such that the shell member 22 slides through the semi-circular shaped aperture 30 and under the tongue 28 during latching. Once the shell member 22 passes the tongue 28, the roles change. The first end 14 functions as a female component when the shell member 22 resiliently returns to its original shape and is allowed to slide back onto the second end 16 (now a male component) and over the tongue 28. As such, the shell member 22 functions as both a male component and female component during operation of the latching mechanism 20 and the collar member 26 functions as both a male component and female component during operation of the latching mechanism 20; that is, the shell member 22 functions as a male component during insertion through the collar member 26 and a female component thereafter when the tongue 28 is seated therein.

Unlocking is achieved by employing graspers to pull the first end 14 forward away from the second end 16 removing the tongue from the shell member 22. The M-shape of the shell member 22 permits it to collapse and move under the tongue 28 and through the collar member 26.

More particularly, the shell member 22 at the first end 14 of the gastric band 10 is generally a half-moon shaped shell with an open, wide end 32 tapering toward a narrow end 34 adjacent the tip 36 of the first end 14. The shell member 22 is substantially hollow and is formed from a material, for example, silicone, which permits compression and expansion thereof.

Referring to FIG. 5a, the shell member 22 is formed with a substantially M-shaped outer surface 23a when viewed from the wide end 32 thereof. That is, the outer surface of the shell member 22 has a substantially M-shaped profile, while the inner surface 23b of the shell member 22 adjacent the wide end 32 has a substantially smooth semi-circular profile. The single M-shaped profile has been found to improve flexibility and control as the shell member 22 is passed through the collar member 26. In addition, the inclusion of the M-shape in the wide end 32 of the shell member 22 permits ease of unlocking, as it will be easier and more controllable for one to compress the shell member 22.

The shell member 22 is slid through the collar member 26 as discussed above. Thereafter, the center 54 of the M-shaped wide end 32 returns to its original shape and fits over the tongue 28. When the gastric band 10 is unlatched, the shell member 22 is pulled forward away from the collar member 26 and the M-shaped shell member 22 permits it to move under the tongue 28 and through the collar member 26. The preformed shape of the shell member 22 not only acts as a guiding feature for the tongue 28 to slide over the shell member 22 during unlocking, but will also allow the shell member 22 to more easily slide back through the aperture 30 of the collar member 26.

An aperture 38 is formed within the tab 24 adjacent the tip 36 of the first end 14 and the narrow end 34 of the shell member 22. The aperture 38 is shaped and dimensioned for receipt of a suture or grasper commonly used in the installation of gastric bands. In addition, the tab 24 is formed with protrusions 39 assisting in grabbing the tab 24 during locking and unlocking.

Also at the first end 14, but on the opposite side of the shell member 22 from the aperture 38 and adjacent the wide end 32 of the shell member 22 is a rearwardly extending gripping member 51. The gripping member 51 is shaped and dimensioned to permit dual directional access for locking and unlocking of the latching mechanism 20. More particularly, the gripping member 51 includes protrusions 56 along the top and bottom surfaces 53, 55 thereof. These protrusions facilitate gripping thereof along a first directional orientation. The gripping member 51 is further formed with an "hour glass" shape having a reinforced central section 57. The reinforced central section 57 allows for gripping in a second directional orientation.

Secure fastening of the shell member 22 with the collar member 26 is achieved by ensuring that after the shell member 22 compresses while passing through the collar member 26, the shell member 22 returns to its original shape and the wide end 32 of the shell member 22 abuts with the first edge 46 of the collar member 26.

Latching is further enhanced by providing the collar member 26 with a tongue 28 extending from the collar member 26 away from the tip 50 of the second end 16. The tongue 28 is shaped and dimensioned to seat within the wide end 32 of the shell member 22 after the shell member 22 has passed through the collar member 26 and the gastric band 10 is tensioned as the first and second ends 14, 16 are drawn toward each other with the shell member 22 straining to move back through the collar member 26 toward an unlatched positioned. With this in mind, the tongue 28 may be downwardly oriented such that it slides with the shell member 22 in a convenient and reliable manner. The tongue 28 may be distinctly colored to provided an indication as to whether the latching mechanism 20 is properly locked.

Gripping of the second end 16 is further enhanced through the provision of a forward facing gripping member 58, that is, a gripping member facing the tip 50 of the second end 16. The forward facing gripping member 58 is shaped and dimensioned to permit dual directional access for locking and unlocking of the latching mechanism 20. More particularly, the gripping member 58 includes protrusions 59 along the top and bottom surfaces 62, 64 thereof. These protrusions 59 facilitate gripping thereof along a first directional orientation. The gripping member 58 is further formed with an "hour glass" shape having a reinforced central section 60. The reinforced central section 60 allows for gripping in a second directional orientation.

The gripping member 58 is shaped and dimensioned to receive and center the shell member 22 as it passes through the collar member 26. The gripping member 58 also assists in compressing the shell member 22 as it passes through the collar member 26.

In accordance with a preferred embodiment of the present invention, the gastric band is a balloon-type gastric band as shown in FIGS. 11 to 16. With this in mind, the gastric band 410 is generally composed of a reinforcing belt 412 to which an elongated balloon 414 is secured. The belt 412 includes a first end 416 and a second end 418 to which the first and second latching members 422, 426 are respectively secured. The belt 412 further includes an inner surface 428 and an outer surface 430. The outer surface 430 is substantially smooth and forms a substantial portion of the outer surface 431 of the gastric band 410 when it is secured about a patient's stomach. The inner surface 428 of the belt 412 is shaped and dimensioned for attachment to the outer surface 438 of the balloon 414.

With regard to the balloon 414, it also includes a first end 432, a second end 434, an inner surface 436 and an outer surface 438. The inner surface 436 is substantially smooth and is shaped and dimensioned for engaging the patient's stomach when the gastric band 410 is secured thereto. The outer surface 438 of the balloon 414 is shaped and dimensioned for coupling with the inner surface 428 of the belt 412.

Figure 15:
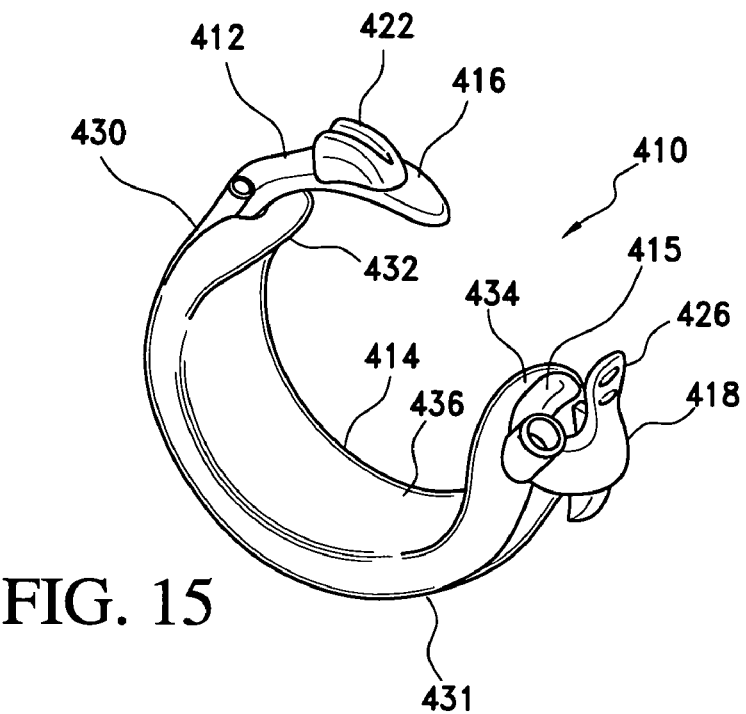
FIGS. 15 and 16 respectively show a perspective view of a gastric band and a cross sectional view of the gastric band in accordance with an alternate embodiment of the present invention.
Figure 16:
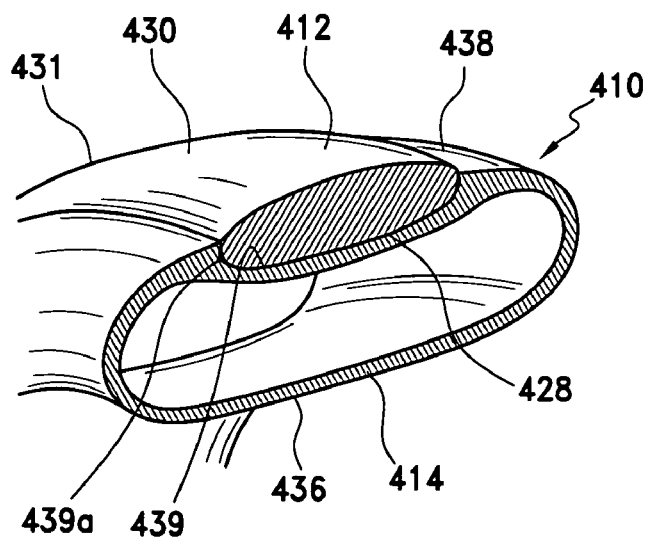

Referring to FIGS. 11 to 16, the belt 412 and balloon 414 may be respectively coupled by either overmolding or separate molding with subsequent adhesive bonding (similar numerals are used for the different embodiments). Regardless of the manufacturing technique, the outer surface 438 of the balloon 414 is formed with a groove 439 shaped and dimensioned for receiving the belt 412. Referring to FIGS. 15 and 16, wherein the belt 412 is adhesively bound to the balloon 414, the groove 439 is formed with a glue gap 439*a* shaped and dimensioned for receipt of a small amount of adhesive without adversely affecting the position of the belt 412 within the groove 439.

Figure 17:
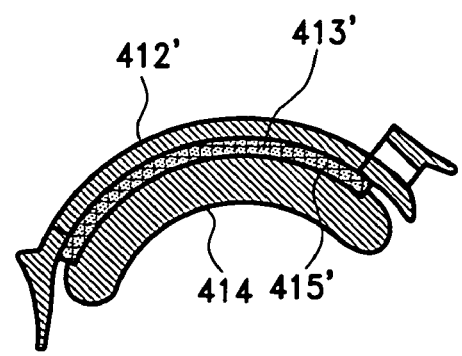
FIG. 17 is a cross sectional view of a gastric band in accordance with another embodiment of the present invention.
Figure 18:
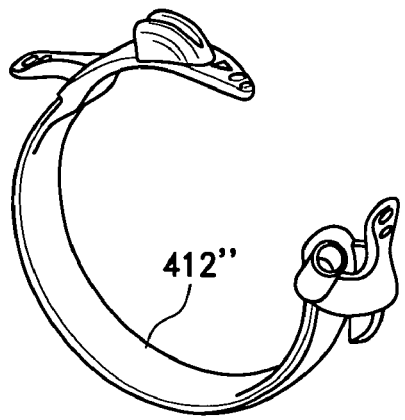
FIGS. 18, 19, 20 and 21 respectively show a perspective view of a belt, a perspective view of a balloon, a cross sectional view of a gastric band and a perspective view of the gastric band in accordance with yet another embodiment of the present invention.
Figure 19:
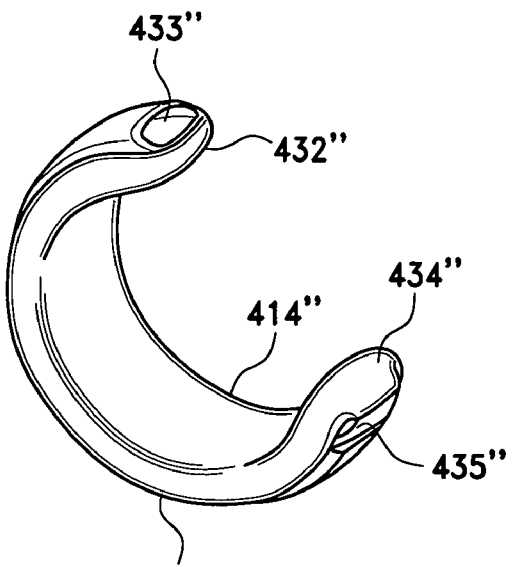
Figure 20:
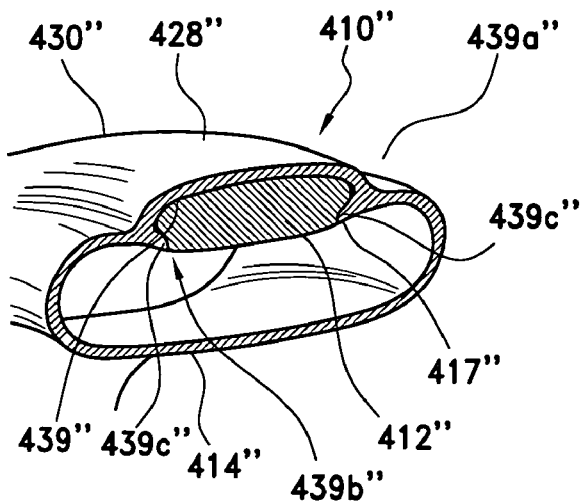
Figure 21:
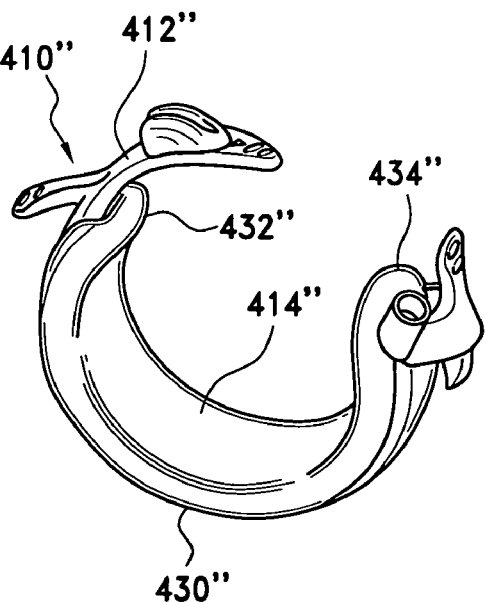

In accordance with an alternate embodiment, and with reference to FIG. 17, it is contemplated the balloon 414' and the belt 412' may be coupled by adding a layer of uncured material 413' (similar in composition to components) between the balloon 414' and belt 412', and curing them together. In addition, a layer of reinforcing structure 415' (mesh, dissimilar material, or higher durometer silicone material) is contained within the layer of uncured material 413'. This reinforcing structure 415' is encapsulated within the device upon assembly and curing, and provide additional structure or different mechanical properties to the product.

In addition, and with reference to FIGS. 18 to 21, yet a further gastric band 410" construction is contemplated in accordance with the present invention. In accordance with this embodiment, the belt 412" is secured along an internal surface 417" of the balloon 414", with the outer surface 428" of the balloon 414" forming the exposed outer surface 430" of the gastric band 410". As with the embodiments disclosed above, the internal surface 417" is formed with a groove 439" shaped and dimensioned for receiving the belt 412". Secure positioning of the belt 412" within the groove 439" is achieved through provision of a glue gap 439*a*" along the groove 439" and a retaining snap 439*b*" along the length of the groove 439". The glue gap 439*a*" is substantially similar to that employed in accordance with the embodiment disclosed with reference to FIGS. 16 and 17.

As to the retaining snap 439*b*", the groove 439" is constructed with opposed, inwardly directed protrusions 439*c*" shaped and dimensioned to engage the belt 412", and temporarily retain the belt 412" within the groove 439", while the glue used to couple the belt 412" and balloon 414" cures during the gluing operation. More particularly, the inwardly directed protrusions 439*c*" are shaped and dimensioned to wrap about the belt 412" in a manner holding it within the groove 439*c*".

In accordance with a preferred embodiment, the belt 412" is positioned within the balloon 414" in the following manner. The belt 412" is threaded through one of the balloon openings 433", 435" on either end 432", 434" of the balloon 414". The retaining snap 439*b*, specifically protrusions 439*c*", on the groove 439 of the balloon 414" temporarily hold the components together while they are being glued via a long needle inserted between the balloon 414" and the belt 412". Alternately, it is contemplated the balloon can be overmolded onto the belt.

In accordance with preferred embodiments, and as briefly discussed above, the balloon and belt may be secured together by either adhesive bonding, comolding, overmolding or mechanical connection (for example, coupling sleeves), which secures the balloon and belt in a manner resulting in the coupling of these distinct gastric band components. Where the belt and balloon are overmolded, a plug 415 would be used to close the core outlet in the balloon for the over mold and the plug would be integral to the gastric band structure (see FIG. 14). As those skilled in the art will certainly appreciate, co-molding is essentially the same procedure as overmolding, but materials of different properties are shot in the mold at the same time. As with overmolding, comolding requires a plug to close the core outlet in the balloon.

Regardless of how the product is molded or assembled together, the belt and balloon components may consist of the same materials or different materials (material durometer, fillers such as $BaSO_4$, $TiO_2$, colorants, etc.). In addition, features within the same component (i.e. the locking features or end caps) may vary in composition. These features may be adhered to the rest of the product with adhesive, mechanical fastening (i.e., snap fits), welding, co-molding, or overmolding. Although the belt is disclosed as being secured to an outer surface of the balloon, it is contemplated the belt may be internal or external to the balloon surface or integrated into the balloon, without departing from the spirit of the present invention.

For assembly methods allowing the adherence of different components (that is, adhesive bonding, mechanical connection, overmolding), unique belt and balloon components may be combined to provide variable configurations. For example, belts with different locking mechanisms may be interchanged with balloons of different lengths to provide the possibility of multiple combinations of products.

The balloon 414 is constructed to enhance contact with the stomach wall when applied thereto. With this in mind, and as will be discussed below in greater detail, the balloon 414 is constructed as a precurved, low pressure, high volume balloon. The balloon 414 is constructed to maintain a soft and flexible surface (low pressure) when applied to the stomach tissue. The balloon 414 is also constructed to provide 360 degree coverage to prevent tissue pinching or discontinuities in stomach shape, and, as such, may employ the balloon construction disclosed in commonly owned U.S. patent application Ser. No. 11/182,070, entitled "GASTRIC BAND WITH MATING END PROFILES", filed Jul. 15, 2005, which is incorporated herein by reference. The balloon 414 is further constructed such that it reaches it fully inflated and encircling configuration with minimal "folds". In addition, the balloon 414 is constructed to exhibit no folds or creases (single axis, not dual axis) when all fluid is evacuated therefrom.

With the foregoing in mind, the balloon 414 employed in accordance with a preferred embodiment of the present application is constructed of an elastomeric material. Due to the design of this balloon, it does not inflate or expand in a manner causing high strain in balloon when filled during gastric band adjustment. Rather, the balloon 414 is adapted to receive a large volume of fluid under a relatively low pressure. In this way, the balloon 414 receives fluid during application, but does not inflate or expand in a traditional manner creating strain along the walls of the balloon 414. In other words, when the balloon 414 is filled up to the volume recommended to achieve maximum stomach restriction, there is no expansion of the balloon material. Instead, the balloon 414 fills to some percentage of its total theoretical volume (that is, maximum fill volume). Since the balloon 414 is not filled even close to its maximum fill volume, it remains low pressure, allowing the balloon 414 to conform to the stomach rather than the stomach to a rigid balloon.

In accordance with a preferred embodiment of the present invention, the balloon 414 is designed with a maximum capacity of between approximately 10 cc and approximately 18 cc, and preferably 18 cc, although it will be fully filled for functioning in accordance with the present invention to achieve the smallest stoma size with approximately 9 cc to approximately 12 cc, and preferably 9 cc. By providing a balloon 414, which is not at its capacity when properly filled for functioning, the softness and conformance of the balloon is improved. While specific volumes are disclosed in accordance with a preferred embodiment of the present invention, those skilled in the art will appreciate the filling volumes may be varied without departing from the spirit of the present invention.

In addition, the balloon 414 is fabricated such that it exhibits a curved configuration when unstressed. Although a variety of curvatures are possible within the spirit of the present invention, the curved configuration is designed to offer a radius of curvature of approximately 0.5 inches to approximately 1.5 inches. In addition, it is contemplated the balloon may have a varying radius as it extends about its length. In general, the balloon curvature is designed to approximate the curvature required to bring the first and second latching members 422, 426 into approximation or contact when the balloon 414 is unbiased and left to assume a relaxed configuration. By fabricating the balloon 414 with an inherent curvature, folds created upon the application of fluid are substantially decreased. With this in mind, the belt is similarly pre-curved to reduce folds and approximate the first and second latching members 422, 426.

As those skilled in the art will certainly appreciate, the belt 412 is constructed to have a curvature approximately the same that of the balloon 414 such that undesirable tension between the belt 412 and balloon 414 is reduced. In addition, and in consideration of the precurved nature of the belt 412, the belt 412 readily conforms to the outer surface of the stomach and the belt 412.

Contact with the stomach tissue is further enhanced by providing the balloon 414 with a concave cross-section along the balloons inner surface 436. This cross sectional configuration helps to facilitate evacuation and straightening thereof.

By implementing the structural criteria outlined above, the balloon 414 deflates with no creases or bulges forming on the inner surface 436 of the balloon 414, a low pressure and pre-curved balloon 414 is achieved and the balloon 414 changes shape when it is filling (zip-lock bag filling up). As to the change in shape, the balloon 414 is constructed such that it has a relatively wider and flatter cross section prior to filling along a cross section transverse to the longitudinal axis of the balloon 414. When the balloon 414 is subsequently filled during application to the stomach of a patient, the transverse cross sectional shape of the balloon 414 changes to that of a rounder balloon exhibiting a narrower cross section with a greater distance between the inner and outer surfaces 436, 430 thereof. With this in mind, it is further contemplated that the balloon cross section may be molded in a rounded rectangular shape, wherein the "corners" provide support, distribute the change in shape and reduce folds. By providing a balloon which is wide and flat prior to filling, the distance between the inner surface of the balloon and the belt is reduced. This reduces the ultimate profile of the gastric band and improves the ability of the gastric band to be readily delivered for deployment.

As those skilled in the art will certainly appreciate, a supply tube is used to connect the internal cavity of the balloon of the gastric band with a pressurized fluid source. The utilization of the tube with a remote fluid source allows for controlled inflation and deflation of the balloon in a predetermined manner. The exact position of the tube is important in that the surgeon does not want tubing to be a visual obstruction during locking and/or other manipulation of the gastric band. In addition, once placement of the gastric band is complete, the tube should not cause irritation to surrounding tissue (for example, sticking directly into the liver or spleen). Surgeons also do not want to pull the tube through a retro-gastric tunnel, since they cannot easily see if the tissue is being damaged. The tube should also be able to act as a safe grasping location for manipulation of the gastric band, the tube must not kink at the junction to the gastric band and prevent fluid flow, and the tube location should facilitate passage of the band through a small trocar.

With this in mind, and in accordance with various preferred embodiments of the present invention, different tube placements are shown with reference to FIGS. 22 to 31. As each these various embodiments show, the tube is positioned at an end of the gastric band. By positioning the tube at an end of the gastric band it has been found that forces upon the tube, gastric band, and, ultimately the stomach, are reduced. This positioning also enhances the ability of the tube and gastric band to flex for insertion and expand to its original shape upon deployment.

Figure 22:
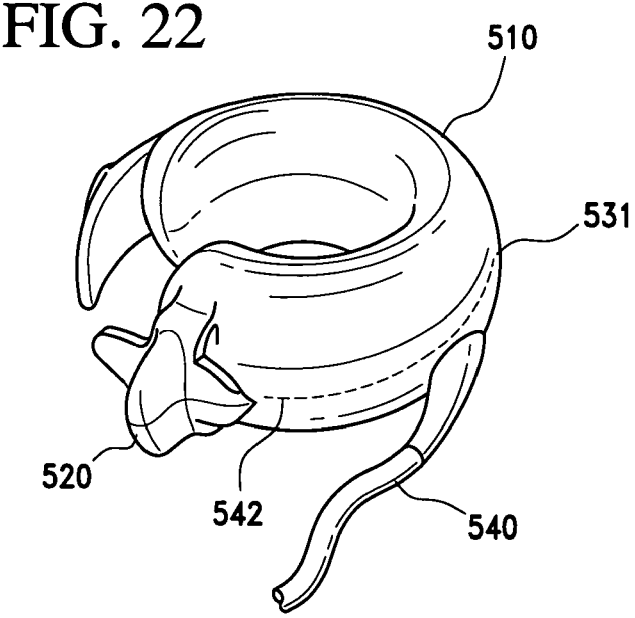
FIGS. 22 to 31 show various embodiments of a balloon type gastric band with differing supply tube locations.

Referring to FIG. 22, the tube 540 is oriented to exit the gastric band 510 from the outer surface thereof. In accordance with a preferred embodiment of this design, the tube 540 is positioned such that is comes out the outer surface 531 of the gastric band 510 just below a longitudinally extending midline 542 of the gastric band 510. The tube 540 is positioned so that is placed clear of the latching mechanism 520 and obliquely angled relative to the longitudinal axis (in accordance with a preferred embodiment at an angle of approximately 34°) of the gastric band 510 to allow easy insertion through a trocar.

Figure 23:
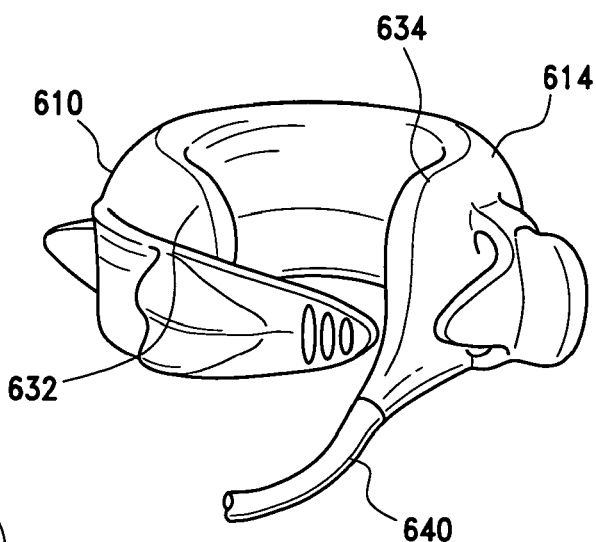

Referring to FIG. 23, the tube 640 is molded on the second end 634 of the balloon 614. In particular, the tube 640 is molded at the very end of the balloon 614, and is integrated into the balloon shape. As with the prior embodiment, the tube 640 is obliquely oriented relative to the longitudinally axis of the gastric band 610 and is similarly positioned below a longitudinally extending midline of the gastric band 610. The offset allows for the balloon ends 632, 634 to meet without interference from the tube 640.

Figure 24:
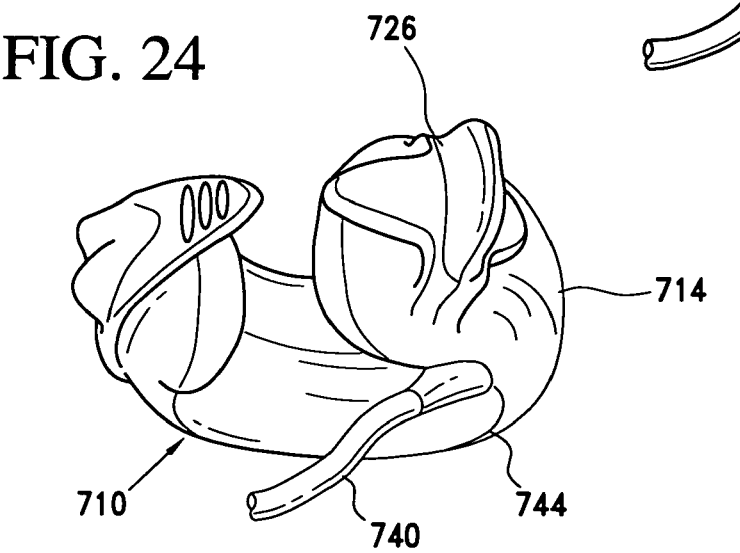

A further embodiment is shown with reference to FIG. 24, wherein the tube 740 exits the balloon 714 off a lateral side 744, that is, a very bottom surface, of the balloon 714 as it is positioned within the patient. The tube 740 entry point is substantially aligned with the second latching member 726 relative to the longitudinal axis of the gastric band 710. As with the prior embodiments, the tube 740 is obliquely oriented relative to the longitudinally axis of the gastric band 710.

Figure 25:
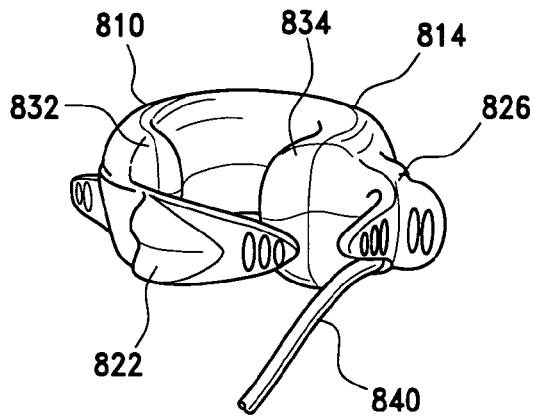
Figure 26:
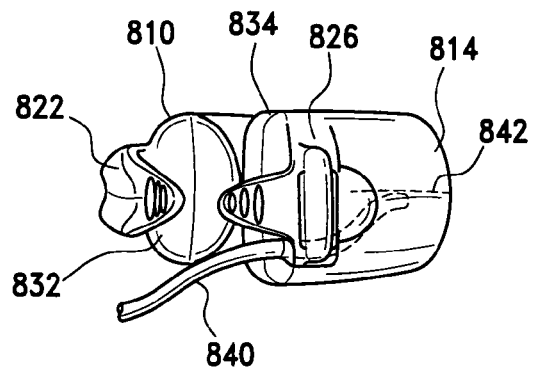

As shown in FIGS. 25 and 26, the tube 840 connection is integrated into one of the sides of the latching members. In accordance with the disclosed embodiment, it is integrated into the second latching member 826, although it is contemplated it could be integrated with the first latching member 822 without departing from the spirit of the present invention.

The tube 840 enters the second latching member 826 and extends therethrough into the body of the balloon 814. Once the tube 840 is inside the body of the balloon 814, it angles to the centerline (or midline 842) of the balloon 814 for even filling of saline. The tube 840 is also obliquely oriented relative to the longitudinally axis of the gastric band 810 and is similarly positioned below a longitudinally extending midline 842 of the gastric band 810. The offset allows for the balloon ends 832, 834 to meet without interference from the tube 840.

Figure 27:
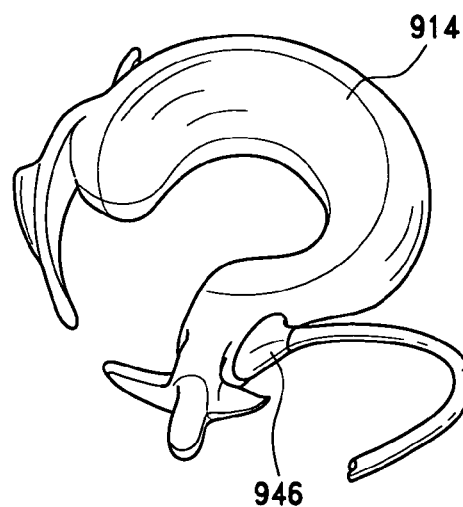
Figure 28:
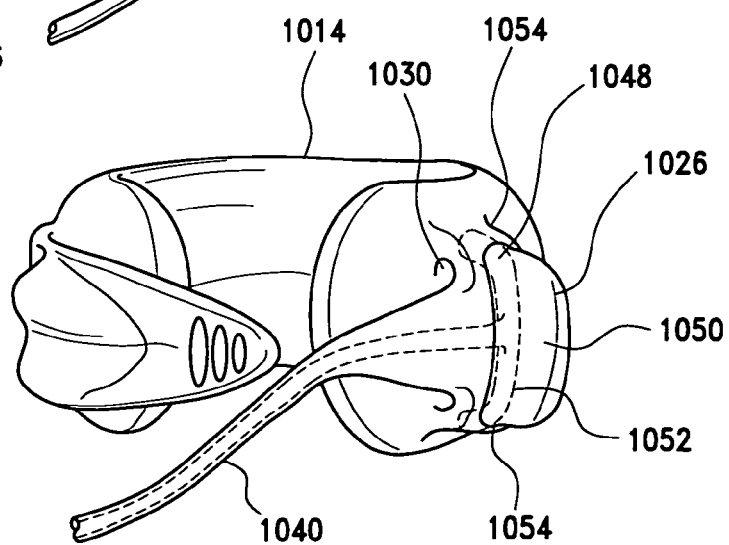

Yet other embodiments are shown respectively with reference to FIGS. 27 and 28. In accordance with one embodiment as shown in FIG. 27, the tube 940 is molded into the plug 946 used to cap the core portion of the balloon 914. In accordance with the other embodiment as shown in FIG. 28, the tube 1040 is molded as an integral portion of the second latching member 1026. The fluid passageway, therefore, extends through the tube 1040, into passageways 1048 formed in the second latching member 1026 and ultimately into the balloon 1014. More particularly, once the tube 1040 enters into a bridge of the second latching member 1026 (that is, where the second latching member 1026 defines the aperture), it splits into a bifurcated tube 1052 that goes into the balloon 1014 via both walls 1054 of the aperture 1030 of the second latching member 1026.

Figure 29:
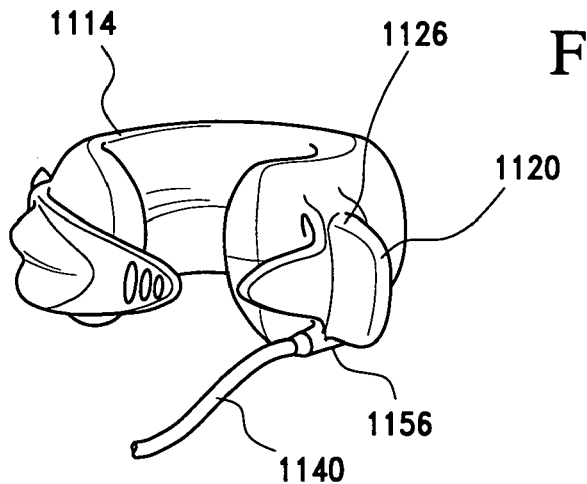
Figure 30:
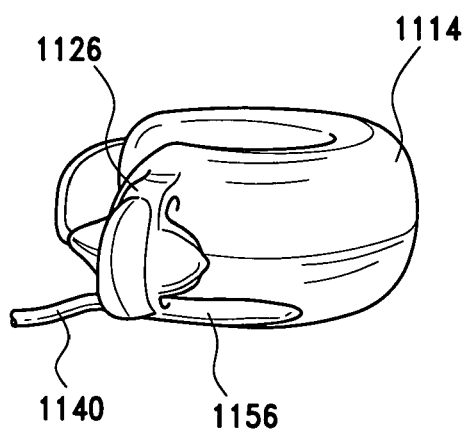

Still another embodiment is shown in FIGS. 29 and 30, wherein the tube 1140 is integrated into one of the sides of the latching mechanism 1120, preferably, the second latching member 1126. The tube 1140 then runs through a gusset 1156 from the back of the second latching member 1126 to allow for a low entry angle into the balloon 1114.

Figure 31:
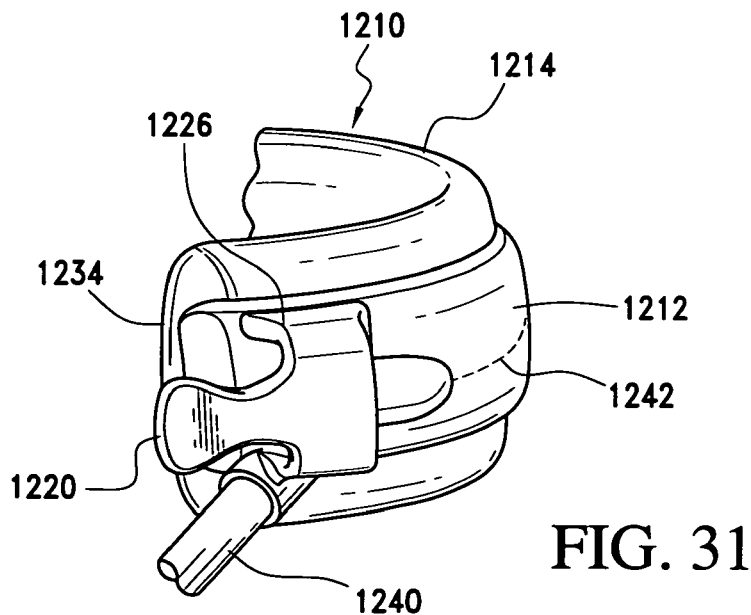
Figure 32:
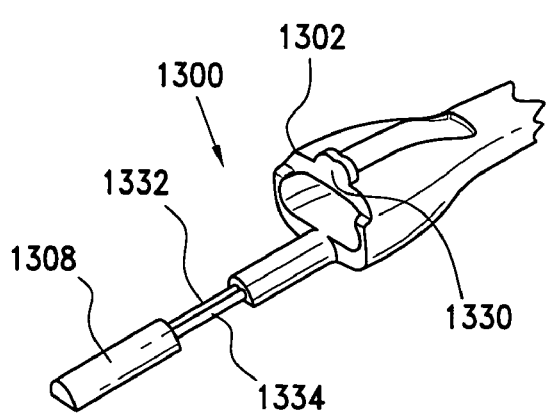
Figure 33:
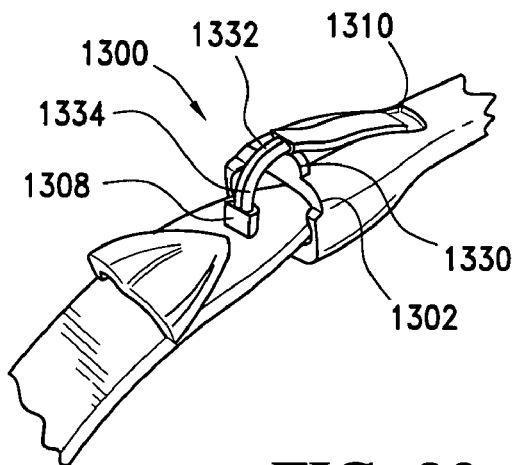

Referring to FIG. 31, the tube 1240 entry is integrated into the belt 1212 (and more particularly, the second latching member 1226) to allow for separate molding of the belt 1212 and balloon 1214. By being attached to the second latching member 1226, the tube 1240 could be used to find the location of the latching mechanism 1220 once the implant has been encapsulated into the fibrous tissue. As with the prior embodiments, the tube 1240 is obliquely oriented relative to the longitudinally axis of the gastric band 1210 and is similarly positioned below a longitudinally extending midline 1242 of the gastric band 1210. The offset allows for the balloon ends 1234 to meet without interference from the tube 1240.

In addition, any of the tubing configurations disclosed with reference to FIGS. 22 through 31 could incorporate some type of strain relief member to reduce fatigue as the tubing flexes back and forth in the body. Such strain relief would be achieved by positioning a length of thicker material at the tubing entry point into the balloon (see for example 1156 on FIG. 29, similarly shown but not called out in FIG. 31). The length of thicker material allows the tubing to take a larger curve as it is bent away from the joint between the tube and the balloon. In other words, this length of material that has been thickened increases the stiffness of the tubing in this region to allow the tubing to flex without kinking and moves the point of flexing further away from the vulnerable joint between the band, balloon, and tubing. The strain relief member would be made preferably of silicone, but other materials (plastics, metals, etc.) could also be used. Also, in all of these embodiments, the tubing to could be connected to either the belt or the balloon by any one of multiple manufacturing methods, such as overmolding or assembling and gluing.

Although the present invention is described for use in conjunction with gastric bands, those skilled in the art will appreciate the above invention has equally applicability to other types of implantable bands. For example, bands are used for the treatment of fecal incontinence. One such band is described in U.S. Pat. No. 6,461,292. Bands can also be used to treat urinary incontinence. One such band is described in U.S. Patent Application Publication No. 2003/0105385. Bands can also be used to treat heartburn and/or acid reflux. One such band is described in U.S. Pat. No. 6,470,892. Bands can also be used to treat impotence. One such band is described in U.S. Patent Application Publication No. 2003/0114729.

Referring to FIGS. 1 and 2, the extender 100 includes an elongated body member having a first end 102 and second end 104. The first end 102 includes an open recess 106 shaped and dimensioned to receive the tab 24 of the first latching member 22 at the first end 14 of the gastric band 10. The first end 102 of the extender 100 is further provided with a tether strap 108. The tether strap 108 is shaped and dimensioned for passage through the aperture 38 formed in the tab 24 and ultimate attachment within a coupling indent 110 formed in the outer surface of the first end 102 of the extender 100. In this way, the tether strap 108 extending from the extender 100 loops through the tab 24 readily coupling the first end 102 of the extender 100 the first latching member 22 for selective attachment and detachment.

The second end 104 of the extender 100 includes a gripping section 112 shaped and dimensioned to facilitate gripping thereof as the extender 100 is passed through the collar member 26 and the gastric band 10 is applied around a patient's stomach. In addition, there is a suture loop 105 for compatibility with Goldfinger instruments 150 as discussed above and the gripping section, or flat end, 112 of the extender 100 is compatible with other band passing devices. Between the first end 102 and the second end 104 of the extender 100 is formed a laterally extending retention member 114. The retention member 114 is semi-circular when viewed along a planar, transverse cross section. The retention member 114 tapers to widen as it extends toward the first end 102 of the extender 100 in a manner creating a surface over which the collar member 26 may slide during latching for interim attachment of the extender 100 to the collar member 26. The taper creates an engagement surface 118 which holds the collar member 26 between the enlarged first end 102 of the extender 100 and the retention member 114 when the first end 102 of the extender 100 is temporarily latched to the collar member 26.

Although an extender with a recess and retention member in accordance with a preferred embodiment is disclosed above, the extender may take other forms without departing from the spirit of the present invention. For example, and in accordance with another preferred embodiment shown with reference to FIG. 9, the extension member 200 includes an elongated body member having a first end 202 and second end 204. The first end 202 includes an enclosed, pocket recess, more particularly a pocket, 206 shaped and dimensioned to fully receive the tab 24 of the first latching member 22 at the first end 14 of the gastric band 10. The first end 202 of the extension member 200 is further provided with a tether strap 208. The tether strap 208 is shaped and dimensioned for passage through the aperture 38 formed in the tab 24 and ultimate attachment within a coupling indent 210 formed in the outer surface of the first end 202 of the extension member 200. In this way, the first end 202 of the extension member 200 may be readily and selectively secured and detached from the first latching member 22.

The second end 204 of the extension member 200 includes a series of protrusions 212 shaped and dimensioned to facilitate gripping thereof as the extension member 200 is passed through the collar member 26 and the gastric band 10 is applied around a patient's stomach. The second end 204 also includes a suture loop 205 extending therefrom. Between the first end 202 and the second end 204 of the extension member 200 is formed a laterally extending retention member 214. The retention member 214 includes first and second engagement members 216, 218. The engagement members 216, 218 are tapered to widen as they extend toward the first end 202 of the extension member 200 in a manner creating a surface over which the collar member 26 may slide during latching for interim attachment of the extension member 200 to the collar member 26 prior to complete latching of the gastric band 10 latching mechanism 20 (after which the extension member 200 is detached from the gastric band 10). The taper creates opposed engagement surfaces 220, 222 which hold the collar member 26 between the enlarged first end 202 of the extension member 200 and the engagement members 216, 218 when the first end 202 of the extension member 200 is temporarily latched to the collar member 26.

Regardless of the extender construction utilized in accordance with a gastric band, it is important the extender be readily accessed for removal with little possibility for error. The two key issues in removal of an extender revolve around a surgeon's ability to identify the extender, in particular, that part of the extender requiring manipulation for removal thereof, and proceed to remove the extending in accordance with the removal mechanism employed. With this in mind, various embodiments for ensuring clear visualization and convenient cutting have been developed. Any of the embodiments described below can incorporate a visual indicator such as color (on either the entire extender, the tether strap, or the only the region to be cut) or a visible suture to indicate to the surgeons that this is a separate component from the gastric band that should be removed. In addition, these embodiments also provide various means in which the extender may be attached to the gastric band (tether strap, suture, etc.).

More particularly, and with reference to FIGS. 32, 33, 35 and 36, the extender 1300 adjacent the first end 1302 thereof or the tether strap 1508, 1608 of the extender 1500, 1600 is provided with one or more bumps or ramps 1330, 1530, 1630 at a location adjacent the open coupling indent, or pocket, 1310 into which the tether strap 1308, 1508, 1608 of the extender 1300, 1500, 1600 is to be positioned. By providing a bump or ramp 1330, 1530, 1630 at this position (on either the first end of the extender or on the tether strap), the tether strap 1308, 1508, 1608 is held above the first end 1302 and the surgeon is able to readily visualize the location of the tether strap 1308, 1508, 1608. The bump or ramp 1330, 1530, 1630 location is at a position adjacent the point at which the tether strap 1308, 1508, 1608 is to be cut for removal of the extender 1300, 1500, 1600 and, therefore, provides the surgeon a visual indicator as to the cut location. In accordance the embodiment shown with reference to FIG. 35, two bumps 1530a, 1530b wrap completely around the tether strap 1508 and define an area at which a surgeon should cut the tether strap 1508.

In addition to improving visualization of the tether strap, in each embodiment the bumps or ramp raise the tether slightly above the gastric band, increasing the space between the tether and the gastric band to provide an improved passageway for position scissors therein for cutting of the tether and ultimate removal of the extender. Visualization of the cutting location in accordance with this embodiment is enhanced by providing a gap or a notch 1332, 1432, 1532 along the tether strap 1308, 1408, 1508 (see FIGS. 32, 33, 34 and 35). In particular and with reference to FIGS. 32, 33 and 43, the suture loop at the second end of the extender 1300, 2200 is continued throughout the body of the extender 1300, 2200 with the suture 1334, 2234 extending through the tether strap 1308, 2208 and functioning as a reinforcing member. However, a portion of the suture 1334, 2234 is exposed along the tether strap 1308, 2208 at a predetermined location such that when the tether strap 1308, 2208 is passed through aperture 38 of the gastric band tab 24 and wrapped about the gastric band 10 to secure the two components together, the gap 1332, 2232 is positioned at the desired location for cutting.

Figure 34:
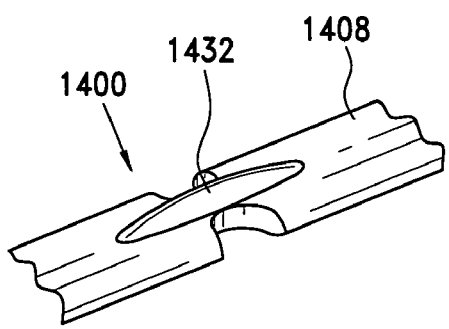
Figure 35:
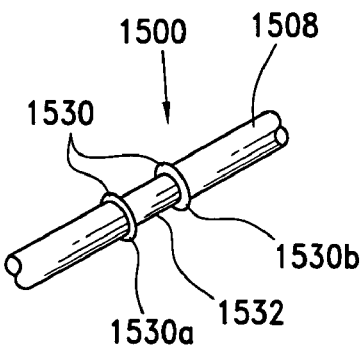
Figure 36:
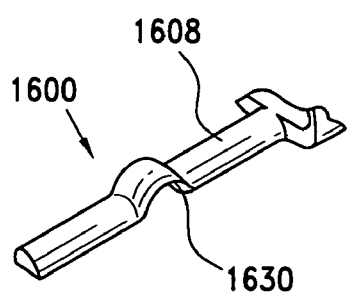

Similarly, and as is seen if FIGS. 34 and 35, the tether strap 1408, 1508 may have a localized region that is smaller than the remainder of the tether strap 1408, 1508 allowing for cutting in a single step. More particularly, the localized region is preferably a notch 1432, 1532 formed along the tether strap 1408, 1508. In addition, because the gap or notch 1432, 1532 is readily differentiated based upon its physical appearance from the remainder of the tether 1408, 1508, a surgeon may easily identify the location requiring cutting. It is contemplated either the notch or gap design could be used in conjunction with the bump described above with reference to FIGS. 32, 33, 36, 42 and 43, although these designs could certainly be employed without the bump where certain design considerations dictate.

Figure 37:
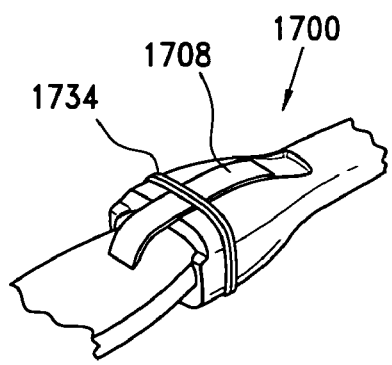

Other embodiments are disclosed with reference to FIGS. 37, 39 and 40. These embodiments employ a reinforcing member, for example, a suture 1734, 1934 to aid in the connection of the extender 1700, 1900 to the tip of the gastric band. In one application (see FIG. 37), the suture 1734 holds the tether strap 1708 down upon the body thereof. As such, and rather than cutting the tether strap 1708 itself as disclosed above with reference to the various embodiments, the securing suture 1734 is cut to thereby release the tether strap 1708 for removal of the extender 1700. Alternately, the suture may be used to tie down the strap and as such, secure the tether to the extender without the assistance of adhesive. Although a suture is disclosed as a reinforcing member in accordance with a preferred embodiment, other reinforcing structures, for example, mesh, may be used within the spirit of the present invention.

In another related embodiment shown in FIG. 39 and 40, the suture material of the suture loop 1905 is extended to run the length of the extender 1900 such that the suture material 1934, extends from the first end 1902 of the extender 1900 (substantially replacing the tether of the prior embodiments). This allows the extender 1900 to wrap a suture 1934 through an aperture 38 in the tip of the gastric band 10 and engage a projection 1936 extending from the first end 1902 of the extender 1900. In addition to securing the gastric band in a reliable and convenient manner, this embodiment provides additional benefits in that the suture 1934 now has a loop at the first end 1902 and the second end 1904 of the extender 1900. This increases the strength of the extender 1900 because the suture cannot pull out of the extender independent of extender material failure.

Referring to FIG. 38, another embodiment is disclosed. In accordance with this embodiment, the tip 1812 of the gastric band 1810 is seated within the recess 1806 formed in the extender 1800. However, the recess 1806 and the tip 1812 of the gastric band 1810 include a snap feature providing a semi-mechanical locking mechanism between the gastric band 1810 and the extender 1800. Such an embodiment would improve the ability of the extender 1800 to lead and guide the tip 1812 of the gastric band 1810 in concert without twisting or flipping. Such a semi-mechanical locking mechanism could be utilized in conjunction with the other tether securing arrangements as a means for providing redundant securing of the extender to the gastric band. It is further contemplated this embodiment may have suture 1811 around the tip 1812 of the gastric band 1810 and the recess 1806 of the extender 1800 (like FIG. 37) to compress the region where the snap fitting tip 1812 fits within the recess 1806 of the extender 1800. When the surgeon cuts and removes the surrounding suture 1811, they can then expand the flexible silicone extender 1800 over the snap fitting tip 1812 on the front of the tab to separate the extender 1800 from the gastric band 1810 in one piece.

Further and with reference to FIG. 41, a suture 2034 is similarly utilized in securing the extender 2000 to the gastric band. However, the projection 2036 to which the extender 2000 is secured is designed such that it may be peeled away. As such, when it is desired to remove the extender 2000, one need only peel away the projection 2036 to release the extender 2000 and thereby no cutting is required.

Referring to FIG. 42, another embodiment is disclosed. In accordance with this embodiment, the tether 2108 of the extender 2100 is lengthened to allow the glue position 2138 to be moved a forward position on the open recess 2106 extender 2100. This allows the tether 2108 of the extender 2100 to be cut at line 2140 to remove the extender 2100. More particularly, the open recess 2106 includes a forward and 2106a positioned toward the middle of the extender 2100 and a rearward position 2106b positioned near the first end 2102 of the extender 2100. The glue position 2138 is at the forward end 2106a. This is still a one-piece removal, only the length of the location for cutting has changed. This embodiment allows the tether 2108 to bow for improved access with scissors or other tools when the front of the extender is flexed upwardly since the tether is only glued at one end 2106a.

In accordance with yet another embodiment, and with reference to FIG. 43, a flange or stopper 2242 is positioned at a preset point along the length of the tether 2208. This enables positioning of the gap 2232 in the tether 2208 relative to the position of the extender 2200 where the suture 2234 needs to be cut and to avoid having suturing contact with the gastric band hole during band pulling. The stopper 2242 is positioned to engage the tab surrounding the aperture so as to limit the extent to which the tether 2208 may pass therethrough. The portion of the tether 2208 adjacent the stopper 2242 may be tapered and the section that is positioned inside the aperture of the gastric band can be larger in cross section to provide a snug fit with the hole of the gastric band. As with prior embodiments the tether will includes a gap or notched section for identification and cutting thereof. In addition, the suture loop runs fully through the extender and may be utilized by tying it into a knot that is molded within the enlarged section of the stopper so as to improve the strength of the extender tether.

It will become readily apparent to those skilled in the art that the above invention has equally applicability to other types of implantable bands. For example, bands are used for the treatment of fecal incontinence. One such band is described in U.S. Pat. No. 6,461,292 which is hereby incorporated herein by reference. Bands can also be used to treat urinary incontinence. One such band is described in U.S. patent application Ser. No. 2003/0105385 which is hereby incorporated herein by reference. Bands can also be used to treat heartburn and/or acid reflux. One such band is described in U.S. Pat. No. 6,470,892 which is hereby incorporated herein by reference. Bands can also be used to treat impotence. One such band is described in U.S. patent application Ser. No. 2003/0114729 which is hereby incorporated herein by reference.

While the preferred embodiments have been shown and described, it will be understood that there is no intent to limit the invention by such disclosure, but rather, is intended to cover all modifications and alternate constructions falling within the spirit and scope of the invention.

What is claimed:

1. A method of implanting a surgically implantable band, said method comprising the steps of:
   a. providing a band comprising an elongated body member including a first end having a first latching member positioned thereon, and a second end having a second latching member positioned thereon, said first latching member having a suture tab extender extending therefrom, said suture tab extender having a suture attached thereto, said second end having a gripping section positioned thereon shaped and dimensioned to facilitate gripping thereof as the gastric band extender is passed through the second latching member;
   b. positioning said band around an anatomical structure, latching said band around said structure by placing said suture tab extender through said second latching member and thereafter coupling said first and second latching members;
   c. removing said suture tab extender from said band.

2. The method of claim 1 wherein said step of removing said suture tab extender from said band comprises the step of removing said suture tab extender as a single piece.

3. The method of claim 1 wherein said step of placing said suture tab extender through said second latching member comprises pulling said suture tab extender through said second latching member.

4. The method of claim 1 wherein said step of placing said suture tab extender through said second latching member comprises pushing said suture tab extender through said second latching member.

5. The method of claim 1 wherein said step of removing said suture tab extender from said band comprises the step of removing said suture tab extender.

* * * * *